United States Patent

Blakeney et al.

Patent Number: 6,140,026
Date of Patent: Oct. 31, 2000

[54] PHOTOSENSITIVE DIAZONAPHTHOQUINONE ESTERS BASED ON SELECTED CYCLIC ALKYL ETHER-CONTAINING PHENOLICS AND THEIR USE IN RADIATION SENSITIVE MIXTURES

[75] Inventors: Andrew J. Blakeney, Seekonk, Mass.; Arturo N. Medina, Scotch Plains, N.J.; Medhat A. Toukhy, Barrington, R.I.; Lawrence Ferreira, Fall River, Mass.; Alfred T. Jeffries, III, Providence; Ahmad A. Naiini, Warwick, both of R.I.

[73] Assignee: Arch Specialty Chemicals, Inc., Norwalk, Conn.

[21] Appl. No.: 09/456,372

[22] Filed: Dec. 8, 1999

Related U.S. Application Data

[62] Division of application No. 09/019,958, Feb. 6, 1998, Pat. No. 6,040,107.

[51] Int. Cl.[7] ........................................ G03F 7/30
[52] U.S. Cl. ........................ 430/326; 430/165; 430/192; 430/193
[58] Field of Search ..................... 430/325, 326, 430/192, 193, 165

[56] References Cited

U.S. PATENT DOCUMENTS

| | | | |
|---|---|---|---|
| 3,046,117 | 7/1962 | Sus | 430/193 |
| 5,059,507 | 10/1991 | Uetani et al. | 430/192 |
| 5,275,911 | 1/1994 | Toukhy | 430/191 |
| 5,283,155 | 2/1994 | Uetani et al. | 430/192 |
| 5,358,824 | 10/1994 | Tan et al. | 430/192 |
| 5,407,779 | 4/1995 | Uetani et al. | 430/192 |
| 5,436,107 | 7/1995 | Tomioka et al. | 430/192 |
| 5,541,033 | 7/1996 | Blakeney et al. | 430/192 |
| 5,547,814 | 8/1996 | Blakeney et al. | 430/326 |

*Primary Examiner*—John S. Chu
*Attorney, Agent, or Firm*—Ohlandt, Greeley, Ruggiero & Perle, L.L.P.

[57] ABSTRACT

A photosensitive compound comprising at least one o-quinonediazide sulfonic acid ester of a phenolic compound, said esters selected from the group consisting of formula (II):

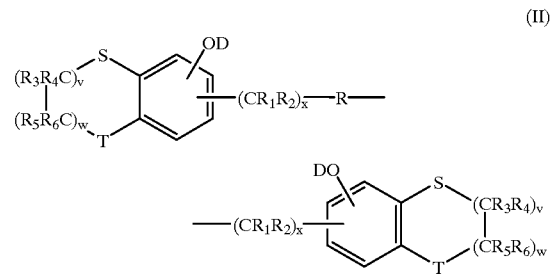

wherein the photosensitive compound is used in a radiation sensitive composition and a process for forming a positive patterned image.

10 Claims, No Drawings

PHOTOSENSITIVE DIAZONAPHTHOQUINONE ESTERS BASED ON SELECTED CYCLIC ALKYL ETHER-CONTAINING PHENOLICS AND THEIR USE IN RADIATION SENSITIVE MIXTURES

This is a division of application Ser. No. 09/019,958 filed Feb. 6, 1998, U.S. Pat. No. 6,040,107.

BACKGROUND OF THE INVENTION

1. Field of the Invention

The present invention relates to certain aromatic ring structures having selected cyclic ether substituents. The present invention also relates to certain photosensitive o-quinonediazide sulfonic acid esters of phenolic compounds containing phenolic rings having cyclic ethers thereon. Still further, the present invention also relates to radiation sensitive mixtures (e.g., those particularly useful as positive-working photo-resists) containing the combination of these photosensitive compounds with alkali-soluble binder resins dissolved in a solvent. And furthermore, the present invention also relates to substrates coated with these radiation sensitive mixtures as well as the process of coating, imaging and developing these radiation sensitive mixtures on these substrates.

2. Description of the Art

Photoresist compositions are used in microlithographic processes for making miniaturized electronic components such as in the fabrication of integrated circuits and printed wiring board circuitry. In these processes, a thin coating or film of a photoresist composition is generally first applied to a substrate material, such as silicon wafers used for making integrated circuits or aluminum or copper plates of printed wiring boards. The coated substrate is then baked to evaporate any solvent in the photoresist composition and to fix the coating onto the substrate. The baked coated surface of the substrate is next subjected to an image-wise exposure of radiation. This radiation exposure causes a chemical transformation in the exposed areas of the coated surface. Visible light, ultraviolet (UV) light, electron beam, ion beam and X-ray radiant energy are radiation types commonly used today in microlithographic processes.

After this image-wise exposure, the coated substrate is treated with a developer solution to dissolve and remove either the radiation-exposed or the unexposed areas of the coated surface of the substrate. In some processes, it is desirable to bake the imaged resist coating before this developing step. This intermediate step is sometimes called post-exposure bake or PEB.

There are two types of photoresist compositions: negative-working and positive-working. When negative-working photoresist compositions are exposed image-wise to radiation, the areas of the resist composition exposed to the radiation become less soluble to a developer solution (e.g., a crosslinking reaction occurs) while the unexposed areas of the photoresist coating remain relatively soluble to a developing solution. Thus, treatment of an exposed negative-working resist with a developer solution causes removal of the nonexposed areas of the resist coating and the creation of a negative image in the photoresist coating, and thereby uncovering a desired portion of the underlying substrate surface on which the photoresist composition was deposited. On the other hand, when positive-working photoresist compositions are exposed image-wise to radiation, those areas of the resist composition exposed to the radiation become more soluble to the developer solution (e.g., the Wolff rearrangement reaction followed by reaction with water of the photoactive compound occurs), while those areas not exposed remain relatively insoluble to the developer solution. Thus, treatment of an exposed positive-working resist with the developer solution causes removal of the exposed areas of the resist coating and the creation of a positive image in the photoresist coating. Again, a desired portion of the underlying substrate surface is uncovered.

Positive-working photoresist compositions are currently favored over negative-working resists because the former generally have better resolution capabilities and pattern transfer characteristics.

After this development operation, the now partially unprotected substrate may be treated with a substrate etchant solution or plasma gases and the like. This etchant solution or plasma gases etch the portion of the substrate where the photoresist coating was removed during development. The areas of the substrate are protected where the photoresist coating still remains and, thus, an etched pattern is created in the substrate material which corresponds to the photomask used for the image-wise exposure of the radiation. Later, the remaining areas of the photoresist coating may be removed during a stripping operation, leaving a clean etched substrate surface. In some instances, it is desirable to heat treat the remaining resist layer after the development step and before the etching step to increase its adhesion to the underlying substrate and its resistance to etching solutions.

End users of photoresists are demanding photoresist formulations that possess better lithographic properties for the fabrication of smaller micro-electronic circuits. The lithographic properties that are critical to these end-users include the following: (1) resolution capabilities in both the micron and submicron ranges without incomplete development in the exposed areas (i.e., scumming); (2) higher thermal image deformation temperatures (e.g., above 120° C.); (3) relatively fast photospeeds; (4) good adhesion to substrate; (5) good developer dissolution rates; (6) wide process latitude; (7) near to absolute vertical profiles (or good contrast) between exposed and unexposed photoresist areas after development; (8) good resistance to etching solutions and plasma etching techniques; (9) reduced tendency to form insoluble particulates; (10) mask linearity; and (11) low metal contamination.

Generally, in the past, efforts to improve one of these lithographic properties may have caused significant decreases in one or more of the other lithographic properties of the photoresist. For example, while photosensitive compounds are essential to obtain the positive images of positive working photoresists, such photosensitive compounds are sometimes not soluble for extended time periods in photoresist formulations. They may also contribute to the degradation of photoresist formulations by chemical reaction. Still further, certain photoactive compounds may contribute to scumming, causing the degradation of the thermal profile, and contributing to the lowering of the thermal deformation temperature of the resist patterns. Selection of a suitable photoactive compound without those weaknesses is a difficult and not a totally predictable task. Accordingly, there is a need for improved photoresist formulations which possess all of these desired properties. The present invention is believed to be an answer to that need.

SUMMARY OF THE INVENTION

Accordingly, one aspect of the present invention is directed to phenolic compounds selected from the group consisting of formula (I):

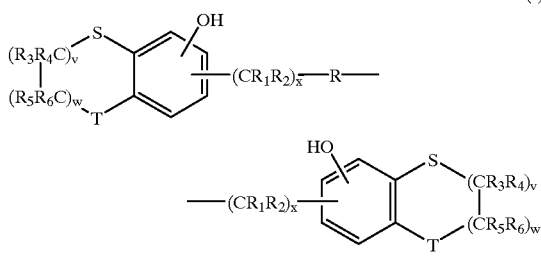
(I)

wherein
$R_1, R_2, R_3, R_4, R_5,$ and $R_6$ are each independently selected from the group consisting of a hydrogen atom and a lower alkyl group having 1–4 carbon atoms;

v and w are each independently selected an integer from 0 to 2 with the proviso that v and w cannot simultaneously be 0;

each S and T are independently selected from the group consisting of oxygen and —$CH_2$—, with the proviso that S and T cannot simultaneously be —$CH_2$—;

x is an integer from 1–4; and

R is a bivalent alkali-soluble moiety selected from the group consisting of formulae (A), (B), (C), (D) and (E):

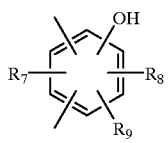
(A)

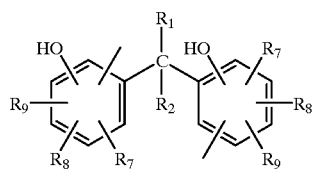
(B)

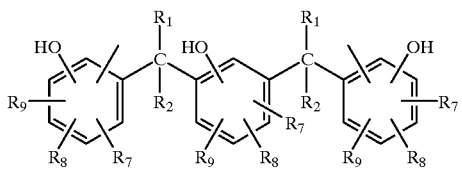
(C)

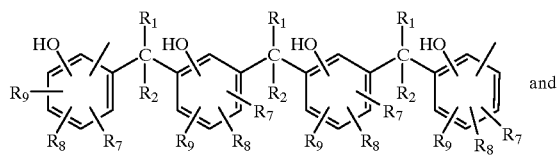
(D)

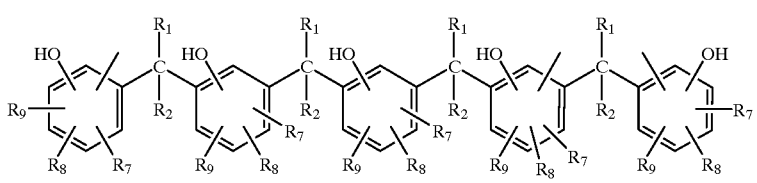
(E)

wherein $R_7$, $R_8$, and $R_9$ are each independently selected from the group consisting of hydrogen, lower alkyl groups having 1–4 carbon atoms, arylalkyl and cycloalkyl.

Another aspect of the present invention is directed to a photosensitive compound comprising at least one o-quinonediazide sulfonic acid ester of a phenolic compound, said phenolic compound containing at least one phenolic ring having a cyclic ether moiety thereon and wherein at least about 75% of the hydroxyl groups on said phenolic rings having the cyclic ether moieties are esterized with an o-quinonediazide sulfonic acid moiety.

Furthermore, another aspect of the present invention is directed to a photosensitive compound comprising at least one o-quinonediazide sulfonic acid ester of a phenolic compound, said phenolic compound having a phenolic backbone having 3 to 7 phenolic rings and 1 to 5 of said phenolic rings having a cyclic ether moiety thereon and at least one of said phenolic rings having no cyclic ether thereon, and wherein at least about 75 percent of the hydroxyl groups on said phenolic rings having the cyclic ether moieties are esterized and less than about 25 percent of the hydroxyl groups on said phenolic rings having no cyclic ether moieties are esterified.

Still another aspect of the present invention is directed to a photosensitive compound comprising at least one o-quinonediazide sulfonic acid ester of a phenolic compound, the esters selected from the group consisting of formula (II):

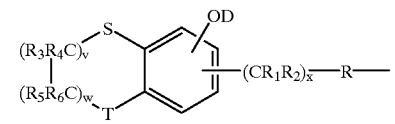
(II)

-continued

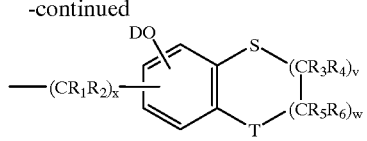

wherein
$R_1, R_2, R_3, R_4, R_5,$ and $R_6$ are each independently selected from the group consisting of a hydrogen atom and a lower alkyl group having 1–4 carbon atoms;

v and w are each an integer from 0 to 2 with the proviso that v and w cannot simultaneously be 0;

each S and T are independently selected from the group consisting of oxygen and —CH$_2$—, with the proviso that S and T cannot simultaneously be —CH$_2$—;

x is an integer from 1–4;

R is a bivalent alkali-soluble moiety selected from the group consisting of formulae (A'), (B'), (C'), (D') and (E'):

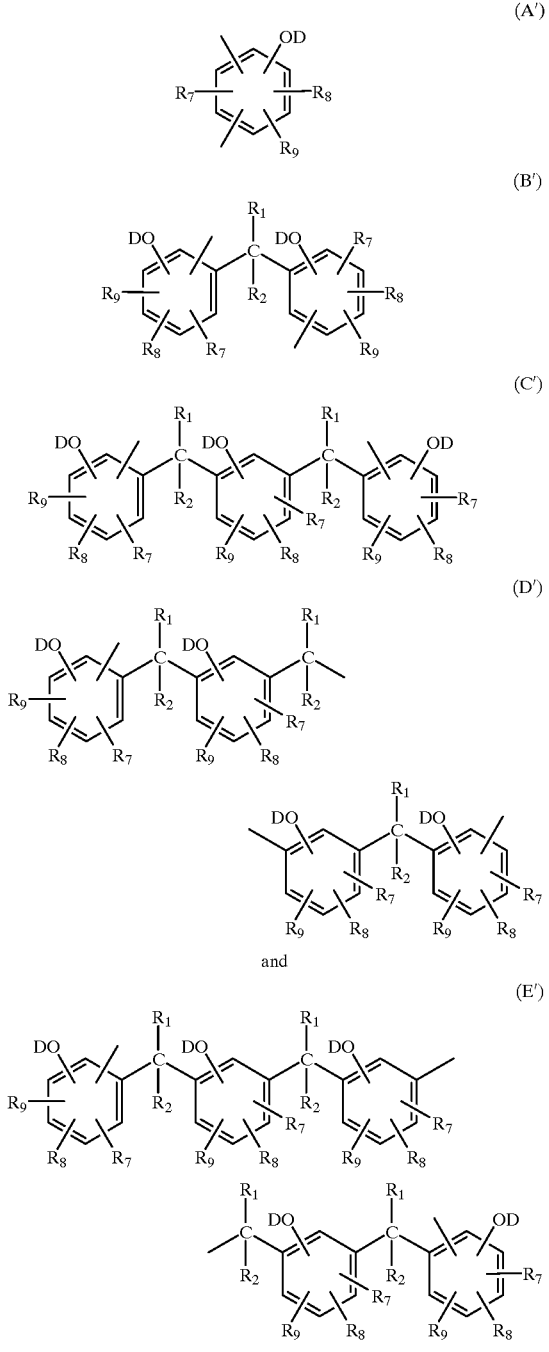

wherein

R$_7$, R$_8$, and R$_9$ are each independently selected from the group consisting of hydrogen, lower alkyl groups having 1–4 carbon atoms, araalkyl and cycloalkyl; and each OD is either hydrogen or is a o-quinonediazide sulfonic acid ester group, subject to the proviso that all of the Ds cannot be hydrogen.

Another aspect of the present invention is directed to a radiation sensitive mixture useful as positive working photoresist, the mixtures comprising an admixture of:

(1) at least one alkali-soluble resin; and (2) at least one photosensitive compound comprising at least one o-quinonediazide sulfonic acid ester as described above.

Still further, the present invention also encompasses the process of coating substrates with these radiation sensitive mixtures and then exposing and developing these coated substrates.

Also further, the present invention encompasses said substrates coated with these radiation sensitive mixtures (both before and after imaging) as novel articles of manufacture.

DESCRIPTION OF PREFERRED EMBODIMENTS

The preferred phenolic compounds of formula (I) are where R$_1$, R$_2$, R$_5$ and R$_6$ are individually selected from hydrogen and methyl groups; both v=0; both w=1; both x=1; and R$_7$, R$_8$ and R$_9$ are independently selected from hydrogen, methyl group and cyclohexyl group. The most preferred compounds of formula I are shown by the following formulae (III), (IV), (V) and (VI):

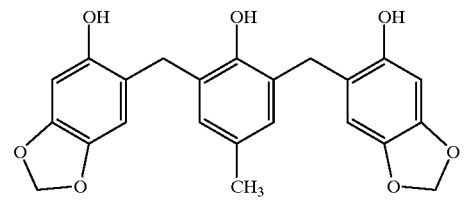

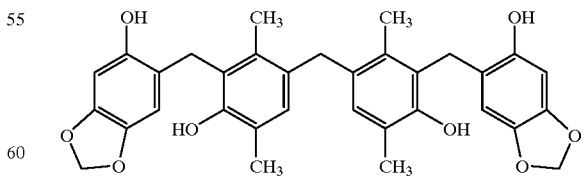

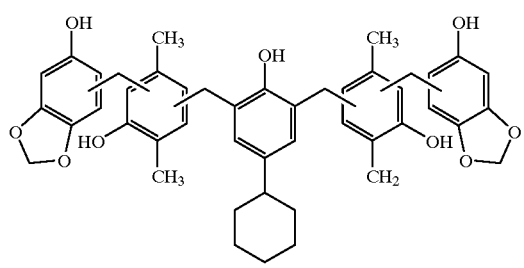

(V)

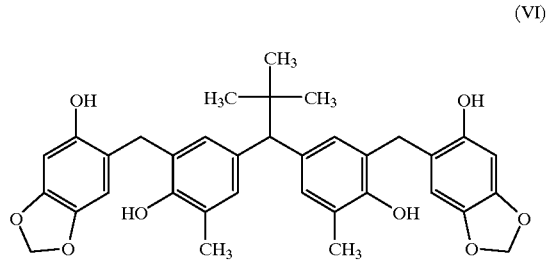

(VI)

The phenolic structure of formula (I) may be converted into photosensitive compounds of formula (II) by reacting those compounds with an o-quinonediazide sulfonyl halide (e.g., napthoquinonediazide sulfonyl halogenide or a benzoquinonediazide sulfonyl halogenide) using conventional reaction conditions.

The most preferred o-naphthoquinone diazide sulfonyl ester moieties are derived from 3-diazo-3,4-dihydro-4-oxonaphthalenesulfonic acid chloride (also known as 1,2-naphthoquinone-(2)-diazo-4-sulfonic acid chloride or Diazo M) or 6-diazo-5,6-dihydro-5-oxonaphthalene-1-sulfonic acid chloride (also known as 1,2-naphthaquinone-(2)-diazo-5-sulfonic acid chloride or Diazo L). These 4- and 5-ester groups or moieties respectively have the following chemical formulae (F) and (G):

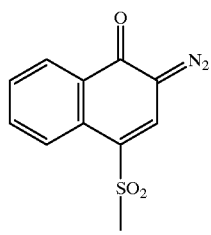

(F)

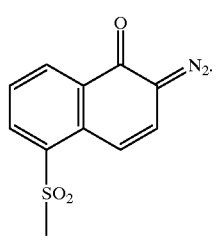

(G)

Other suitable o-quinonediazide sulfonyl moieties are represented by the following formula (H) and (J):

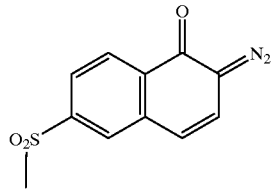

(H)

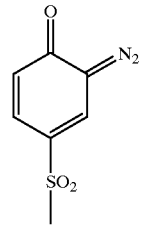

(J)

It is understood that the present invention covers the use of o-quinonediazide sulfonyl moieties singly or in mixtures in the condensation reaction with these compounds of formula (II). Also, the present invention encompasses separate reactions of these compounds with different o-naphthoquinone diazide sulfonyl moieties followed by blending those reaction products together.

This condensation reaction may be carried under any conventional ester condensation conditions. Preferably, the photosensitive ester compounds of formula (II), above, are prepared by first dissolving the sulfonic acid halide precursor, preferably, the sulfonic acid chloride, in a suitable solvent. Suitable solvents include acetone, dioxane, gamma-butyrolactone, methylene chloride, tetrahydrofurfural alcohol and the like. The compounds of formula (II) is then added to this solution. It is advantageous to carry out this reaction in the presence of an acid-scavenging base, such as alkali metal carbonates or bicarbonates, alkaline earth metal carbonates or bicarbonates, tertiary aliphatic amines or pyridine or pyridine derivatives.

The esterification products of this reaction may be recovered from the reaction mixture by any conventional means, preferably by precipitation into acidified water, followed by filtration and drying.

The preferred photosensitive compounds (sometimes also referred to as "photoactive compounds") when said compound is of formula (II) are those where R, $R_1$, $R_2$, $R_3$, $R_4$, $R_5$ and $R_6$ are individually selected from hydrogen and methyl groups; both v=0; both w=1; both x=1; and $R_7$, $R_8$ and $R_9$ are independently selected from hydrogen, methyl group and cyclohexyl group.

More preferably, each D in formula (II), above, and the formulae below are preferably naphthoquinone-(1,2)-diazide-5-sulfonyl; naphthoquinone-(1,2)-diazide-4-sulfonyl or hydrogen, with the proviso that at least two of the D groups are not hydrogen. More preferably, only the hydroxyls on the phenolic rings containing the cyclic ether moiety are esterified.

Specific examples of photosensitive compounds of formula (II) are shown by the following formulae (VII), (VIII), (IX) and (X):

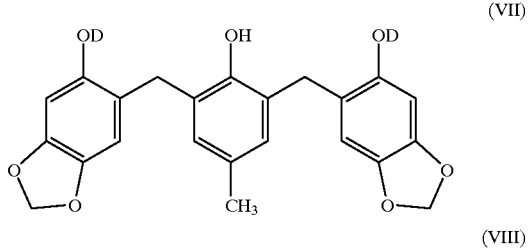

(VII)

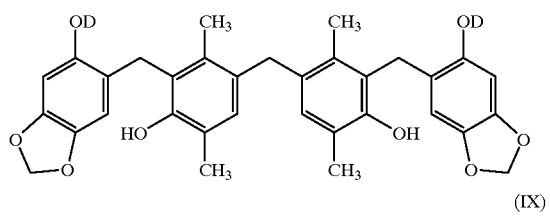

(VIII)

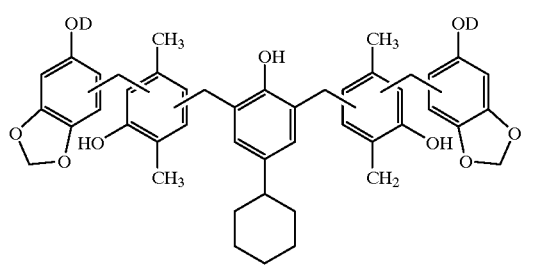

(IX)

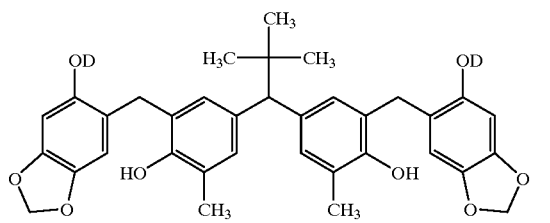

(X)

At least one of the ester compounds of the present invention may be mixed with an alkali-soluble resin or resins to make radiation sensitive mixtures which are useful as positive-working photoresist compositions. The term "alkali-soluble resin" is used herein to mean a resin that will dissolve completely in an aqueous alkaline developing solution conventionally used with positive-working photoresist compositions. Suitable alkali-soluble resins include phenol-formaldehyde novolak resins, cresol-formaldehyde novolak resins, and polyvinyl phenol resins, preferably having a molecular weight (Mw) of about 500 to about 40,000, and more preferably from about 800 to 20,000. The novolak resins are preferably prepared by the condensation reaction of phenol or cresols with formaldehyde and are characterized by being light-stable, water-insoluble, alkali-soluble and film-forming. One preferred class of novolak resins is formed by the condensation reaction between a mixture of meta- and para-cresols with formaldehyde having a molecular weight of about 1,000 to about 10,000. The preparation of examples of such suitable resins is disclosed in U.S. Pat. Nos. 4,377,631; 4,529,682; and 4,587,196, all of which issued to Medhat Toukhy and are incorporated herein by reference in their entireties. Other preferred novolaks are shown in U.S. Pat. Nos. 5,237,037; 5,322,757; and 5,324,620 (issued to Charles Ebersole) and are also incorporated herein by reference in their entireties.

Other photoactive compounds may also be added to the radiation sensitive mixtures of the present invention. These other photosensitive compounds may include o-quinonediazide esters derived from polyhydric phenols, alkyl-polyhydroxyphenones, aryl-polyhydroxyphenones, and the like which can contain up to six or more sites for esterification. Examples of such photoactive compounds are shown in U.S. Pat. Nos. 4,957,846 (Jeffries et al.); 5,312,720 (Jeffries et al.); 5,376,497 (Kawata et al.); 5,429,904 (Nagase et al.); 5,456,995 (Ozaki et al.); 5,456,996 (Ozaki et al.); 5,468,590 (Hashimoto et al.); 5,501,936 (Hosoda et al.); 5,541,033 (Blakeney et al.) and 5,700,620 (Sakaguchi et al.). All of these U.S. patents are incorporated herein by reference in their entireties. The most preferred o-quinonediazide esters are derived from 3-diazo-3,4-dihydro-4-oxonaphthalene-sulfonic acid chloride or 6-diazo-5,6-dihydro-5-oxonaphthalene-1-sulfonic acid chloride. When other photosensitive compounds are used in radiation sensitive mixtures besides the photosensitive compounds of the present invention, the amount of photosensitive compounds of the present invention should be at least about 5% by weight, preferably 10–100% by weight of the total photosensitive compounds present.

Examples of preferred other photosensitive compounds include compounds having the following chemical formulae (K), (L), and (M):

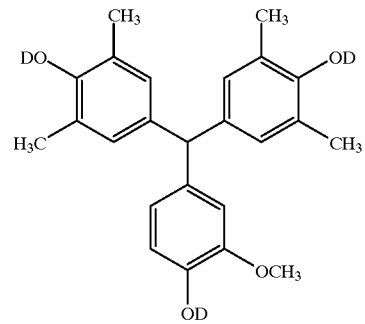

(K)

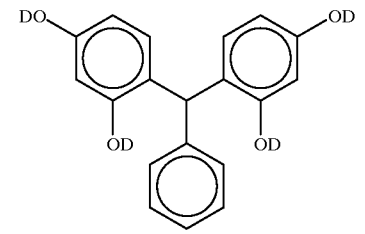

(L)

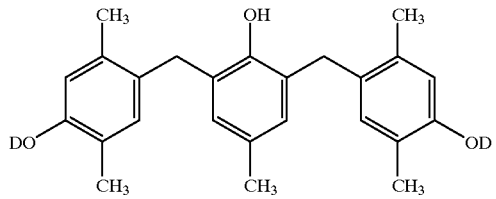

(M)

In each formula, each D is hydrogen or formula (G):

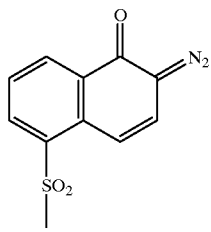
(G)

with the proviso that not all D groups are hydrogen.

The proportion of the photoactive compound in the radiation sensitive mixture may preferably range from about 5 to about 40%, more preferably from about 8 to about 30% by weight of the nonvolatile (e.g., nonsolvent) content of the radiation sensitive mixture.

These radiation sensitive mixtures may also contain conventional photoresist composition ingredients such as solvents, actinic and contrast dyes, anti-striation agents, plasticizers, speed enhancers, and the like. These additional ingredients may be added to the binder resin and photoactive compound before the solution is coated onto the substrate. The proportion of the sum of binder resin and speed enhancers of this present invention in the radiation sensitive mixture may preferably range from about 40 to about 95%, more preferably, from about 70 to 92% of the nonvolatile (e.g., excluding solvents) solids content of the radiation sensitive mixture.

Speed enhancers tend to increase the aqueous alkaline solubility of the photoresist coating in both the exposed and unexposed areas, and thus, they are used in applications where speed of development is the overriding consideration even though some degree of contrast may be sacrificed, i.e., in positive resists while the exposed areas of the photoresist coating will be dissolved more quickly by the developer, the speed enhancers may also cause a larger loss of photoresist coating from the unexposed areas. Speed enhancers that may be used include, for example, picric acid, nicotinic acid or nitrocinnamic acid, as well as poly(monohydric)-phenolic compounds at weight levels of up to 40%, preferably from 10% to 35%, based on the combined weight of resin and photoactive compound. The optimum amount of speed enhancer will depend upon the dissolution rates of binder resin and speed enhancers employed as well as the developer used.

Particularly preferred speed enhancers have chemical formulae (N), (O), (P) and (Q) shown as follows:

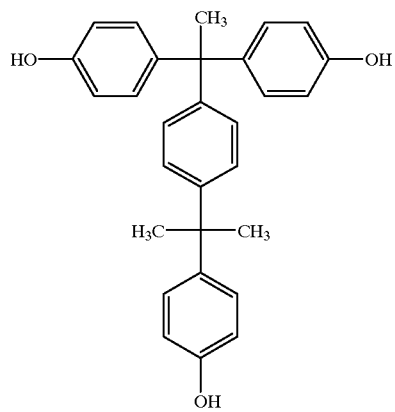
(N)

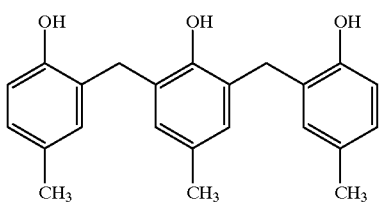
(O)

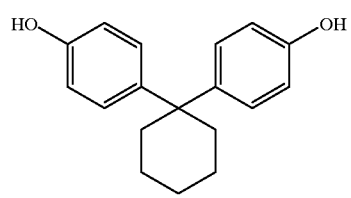
(P)

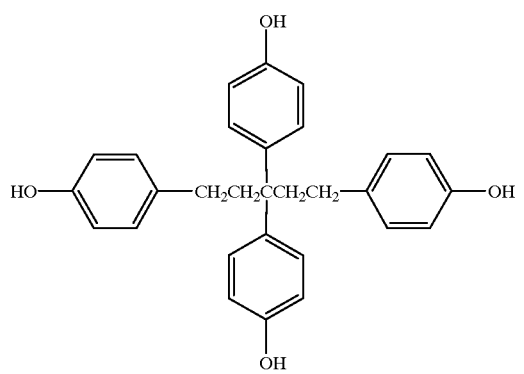
(Q)

The preferred relative amount of speed enhancer in a positive resist is from 0% to about 40%, more preferably from about 15% to about 35% by weight, based on the total weight of all binder resins and speed enhancers in the resist.

The resins, photoactive comopunds and other components are dissolved in a solvent or solvents to facilitate their application to the substrate. Examples of suitable solvents include methoxyacetoxy propane, ethyl cellosolve acetate, ethyl lactate, ethyl 3-ethoxy propionate, 2-heptanone methyl-3-methoxypropionate propylene glycol alkyl ether acetates, or mixtures thereof and the like. Cosolvents such as xylene or n-butylacetate may also be used. The preferred amount of solvent may be from about 50% to about 500%, or higher, by weight, more preferably, from about 100% to about 400% by weight, based on combined resin, photoactive compound and other solid components.

Actinic dyes help provide increased resolution on highly reflective surfaces by inhibiting back scattering of light off the substrate. This back scattering causes the undesirable effect of optical notching, especially on a highly reflective substrate topography. Examples of actinic dyes include those that absorb light energy at approximately 400–460 nm [e.g., Fat Brown B (C.I. No. 12010); Fat Brown RR (C.I. No. 11285); 2-hydroxy-1,4-naphthoquinone (C.I. No. 75480) and Quinoline Yellow A (C.I. No. 47000)] and those that absorb light energy at approximately 300–340 nm [e.g., 2,5-diphenyloxazole (PPO-Chem. Abs. Reg. No. 92-71-7) and 2-(4-biphenyl)-6-phenyl-benzoxazole (PBBO-Chem. Abs. Reg. No. 17064-47-0)]. Another preferred dye is BLANKOPHOR FBW active dye available from Mobay. The use of this dye in positive resists is covered by U.S. Pat. No. 5,275,909, which issued to T. V. Jayaraman and is incorporated herein by reference in its entirety. The amount of actinic dyes may be up to ten percent weight levels, based on the combined weight of resin and sensitizer.

Contrast dyes enhance the visibility of the developed images and facilitate pattern alignment during manufacturing. Examples of contrast dye additives that may be used together with the radiation sensitive mixtures of the present invention include Solvent Red 24 (C.I. No. 26105), Basic Fuchsin (C.I. 42514), Oil Blue N (C.I. No. 61555) and Calco Red A (C.I. No. 26125) up to 10% weight levels, based on the combined weight of resin and sensitizer.

Anti-striation agents or leveling agents level out the resist coating or film to a uniform thickness. In other words, the leveling agent is used to eliminate the formation of striations on the surface of the resist coating once the coating is spun onto the substrate surface. Anti-striation agents may be used up to 5% weight levels, based on the weight of solids in the resist formulation. One suitable class of anti-striation agents is nonionic silicon-modified polymers. A preferred one is TROYKYD 366 made by Troy Chemical Co., Newark, N.J. Another suitable class of anti-striation agents is fluoroaliphatic polymeric ester surfactants. A preferred one is FC-430 FLUORAD made by 3M of St. Paul, Minn. Nonionic surfactants may also be used for this purpose, including, for example nonylphenoxy poly(ethyleneoxy) ethanol; octylphenoxy(ethyleneoxy) ethanol; and dinonyl phenoxy poly(ethyleneoxy) ethanol; polyoxyethylene lauryl ether; polyoxyethylene oleyl ether; polyoxyethylene octylphenyl ether; polyoxyethylene nonylphenyl ether; poly-oxyethylene glycol dilaurate; and polyoxyethylene glycol distearate. Also may be useful are organosiloxane polymers and acrylic acid-containing or methacrylate acid-containing polymers.

Plasticizers improve the coating and adhesion properties of the photoresist composition and better allow for the application of a thin coating or film of photoresist which is smooth and of uniform thickness onto the substrate. Plasticizers which may be used include, for example, phosphoric acid tri-(β-chloroethyl)-ester; stearic acid; dicamphor; polypropylene; acetal resins; phenoxy resins; and alkyl resins up to ten percent weight levels, based on the combined weight of resin and sensitizer.

The prepared radiation sensitive resist mixture, can be applied to a substrate by any conventional method used in the photoresist art, including dipping, spraying, whirling and spin coating. When spin coating, for example, the resist mixture can be adjusted as to the percentage of solids content in order to provide a coating of the desired thickness given the type of spinning equipment and spin speed utilized and the amount of time allowed for the spinning process. Suitable substrates include silicon, aluminum or polymeric resins, silicon dioxide, doped silicon dioxide, silicon resins, gallium arsenide, silicon nitride, tantalum, copper, polysilicon, ceramics and aluminum/copper mixtures. The coating surfaces of these substrates may or may not be primed with a conventional adhesion promoter (e.g., hexamethyldisilazane) before the photoresist coating is applied.

The photoresist coatings produced by the above described procedure are particularly suitable for application to silicon wafers coated with a silicon dioxide or silicon nitride layer such as are utilized in the production of microprocessors and other miniaturized integrated circuit components. An aluminum or aluminum-coated substrates may be used as well. The substrate may also comprise various polymeric resins especially transparent polymers such as polyesters and polyolefins.

After the resist solution is coated onto the substrate, the coated substrate is baked at approximately 70° C. to 125° C. until substantially all the solvent has evaporated and only a uniform radiation sensitive coating remains on the substrate. The coated substrate can then be exposed to radiation, especially ultraviolet radiation, in any desired exposure pattern, produced by use of suitable masks, negatives, stencils, templates, and the like. Conventional imaging process or apparatus currently used in processing photoresist-coated substrates may be employed with the present invention. While ultraviolet (UV) light is the preferred source of radiation, other sources of radiation such as visible light, electron or ion beam and X-ray radiant energy may be used instead.

The exposed resist-coated substrates are preferably subjected to a post exposure bake at a temperature from about 100° C. to about 130° C. from about 30–300 seconds to enhance image quality and resolution. The exposed resist-coated substrates are next developed in an aqueous alkaline solution. This solution is preferably agitated, for example, by nitrogen gas. Examples of aqueous alkaline developers include aqueous solutions of tetramethyl-ammonium hydroxide, sodium hydroxide, potassium hydroxide, ethanolamine, chlorine, sodium phosphates, sodium carbonate, sodium metasilicate, and the like. The preferred developers for this invention are aqueous solutions of either alkali metal hydroxides, phosphates or silicates, or mixtures thereof, or tetramethylammonium hydroxide.

Preferred development techniques include spray development or puddle development, or combinations thereof, may also be used.

The substrates are allowed to remain in the developer until all of the resist coating has dissolved from the exposed areas. Normally, development times from about 10 seconds to about 3 minutes are employed.

After selective dissolution of the coated wafers in the developing solution, they are preferably subjected to a deionized water rinse to fully remove the developer or any remaining undesired portions of the coating and to stop further development. This rinsing operation (which is part of the development process) may be followed by blow drying with filtered air to remove excess water. A post-development heat treatment or bake may then be employed to increase the coating's adhesion and chemical resistance to etching solutions and other substances. The post-development heat treatment can comprise the baking of the coating and substrate below the coating's thermal deformation temperature.

In industrial applications, particularly in the manufacture of microcircuitry units on silicon/silicon dioxide-type substrates, the developed substrates may then be treated with a buffered hydrofluoric acid etching solution or plasma gas etch. The resist compositions of the present invention are believed to be resistant to a wide variety of acid etching solutions or plasma gases and provide effective protection for the resist-coated areas of the substrate. Later, the remaining areas of the photoresist coating may be removed from the etched substrate surface by conventional photoresist stripping operations.

The present invention is further described in detail by means of the following Examples. All parts and percentages are by weight and all temperatures are degrees Celsius unless explicitly stated otherwise.

EXAMPLE 1

Preparation of 2,6-Bis(2-hydroxy-4,5-methylenedioxyphenylmethyl)-4-methyl-1-hydroxybenzene A 250 mL, round bottom flask was charged with 5.0 grams (0.0297 moles) of 2,6-bis(hydroxymethyl)-p-cresol, 41 grams (0.2968 moles) Sesamol, 100 mL methanol, and 17 drops of concentrated sulfuric acid. The mixture was heated to 45–50° C. while stirring, and stirred at 45–50° C. for 3 hours. The product precipitates out of solution during the reaction period. The reaction mixture was cooled to room temperature, and the precipitated product was isolated by filtration, washed with 400 mL of deionized water, and dried in a vacuum oven.

The product was 98.3 area percent pure by HPLC analysis using 60/40 acetonitrile/buffer as eluant. $^1$H NMR and $^{13}$C NMR are consistent with the structure found below (where D=H).

Preparation of DNQ PAC:

2.0 grams (4.897 moles) of 2,6-bis(2-hydroxy-4,5-methylenedioxphenylmethyl)-4-methyl-1-hydroxybenzene, 2.64 grams (9.826 moles) naphthoquinone-(1,2)-diazide-(2)-5-sulfonyl chloride were dissolved in 7 mL of a 50% gamma-butyrolactone/acetone solution. With stirring, triethylamine was slowly added so as to maintain a pH of the reaction mixture between 6.5–7.5. Completion of the reaction was determined by the disappearance of the starting naphthoquinone-(1,2)-diazide-(2)-5-sulfonyl chloride. 2 mL of deionized water were added to hydrolyze residual, unreacted naphthoquinone-(1,2)-diazide-(2)-5-sulfonyl chloride. The reaction mixture was stirred under these conditions for 1 hour. The reaction mixture was then added to a solution of 500 mL water and 1 mL 37% aqueous hydrochloric acid. The resulting precipitate was collected by filtration, washed with fresh deionized water and dried at 25–30° C. under vacuum. The resulting compound was shown by HPLC to be 85–90% selectively esterified only on the two terminal hydroxyls. The structure of this compound corresponds to the following formula (VII'):

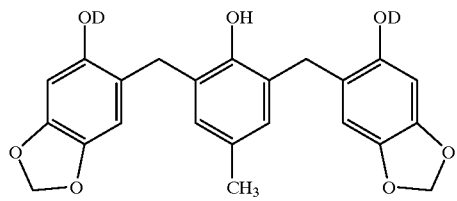

(VII')

where D=

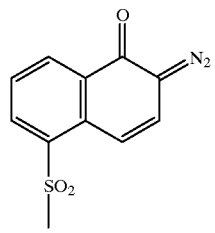

(G)

EXAMPLE 2

Preparation of 2,6-Bis(4-hydroxy-2,5-dimethyl-3-(2-hydroxy-4,5-methylenedioxyphenylmethyl)phenylmethyl)-4-cyclohexyl-1-hydroxybenzene Part A: Preparation of 2,6-bishydroxymethyl-4-cyclohexylphenol A 250 milliliter, round bottom flask was charged with 14.73 grams (83.5 moles) of 4-cyclohexylphenol, and 50.1 mL of 25% aqueous tetramethylammonium hydroxide solution. The mixture was heated with stirring to 45° C. until complete dissolution was obtained. 40.07 grams (493.9 moles) of 37% formalin was added dropwise to the reaction mixture over a period of 90 minutes. The reaction mixture was maintained at 45° C. for 6 hours upon completion of the formalin addition. The reaction was cooled to 40° C. and held overnight at this temperature. The mixture is cooled to room temperature, and the reaction mixture was neutralized by dropwise addition of 9.4 mL of glacial acetic acid, followed by the addition of 30 mL of water. The aqueous phase was removed and the organic phase was dissolved in 85 mL methanol. 60 mL of water were slowly added to the methanol solution. This methanol/water solution was then added dropwise to 1180 mL water to precipitate the product. The resulting yellow precipitate was isolated by filtration, washed with water, and dried in a vacuum oven to constant weight.

Part B: Preparation of 2,6-bis(4-hydroxy-2,5-dimethylphenylmethyl)-4-cyclohexylphenol A 500 milliliter, round bottom flask was charged with 101.84 grams (835 moles) of 2,5-xylenol, and 138 mL methanol. The mixture was stirred until complete dissolution was obtained, and 0.6 grams (6.1 moles) of concentrated sulfuric were added. The solution was heated with stirring to reflux. A solution of 19.74 grams (83.5 moles) of 2,6-bishydroxymethyl-4-cyclohexylphenol ("BHMCHP") in 83 mL of methanol was added dropwise to the reaction mixture over a period of 6 hours. The reaction mixture was refluxed for 2 hours upon completion of the BHMCHP addition.

The reaction mixture was added to a 1000 mL, round bottom flask which contained a solution of 0.34 grams (0.18 moles) potassium hydroxide pellets and 197.4 mL of water at 70° C. and stirred overnight. Stirring was stopped and the phases were allowed to separate. The bottom organic phase was transferred to a 500 milliliter, round bottom flask. Water, methanol and unreacted xylenol were removed from the mixture by atmospheric distillation. When the pot temperature reached 240° C. the contents of the flask were cooled to 100° C. under a nitrogen atmosphere. Residual xylenol was removed by vacuum distillation. Vacuum distillation continued until the pot temperature reached 240° C., and then cooled to room temperature.

The product was a mixture of 2 isomers. Combined, these isomers were 100 area percent pure by HPLC analysis using 80/20 acetonitrile/buffer as eluant.

Part C: Preparation of 2,6-bis(4-hydroxy-3-(N,N-dimethylaminomethyl)-2,5-dimethylphenylmethyl)-4-cyclohexylphenol A 250 milliliter, round bottom flask was charged with 7.69 grams (256 moles) of paraformaldehyde, 35 mL ethanol and 23.08 grams (204 moles) of 40% aqueous solution of dimethylamine. The mixture was heated with stirring to 75° C., and held at 75° C. for 30 minutes, or until complete dissolution was obtained. A solution of 10.49 grams (23.6 mmoles) of 2,6-bis(4-hydroxy-2,5-dimethylphenylmethyl)-4-cyclohexylphenol in 31.4 mL of ethanol (which had been previously filtered through filter paper) was added dropwise to the reaction mixture at 75° C. over a period of 150–180 minutes. The reaction mixture was held at 75° C. for 90 minutes upon completion of the 2,6-bis(4-hydroxy-2,5-dimethylphenylmethyl)-4-cyclohexylphenol addition. The mixture was cooled to room temperature to precipitate the product. The precipitated product was isolated by filtration and dried in a vacuum oven.

Part D: Preparation of (2,6-bis(4-acetoxy-3-(acetoxymethyl)-2,5-dimethylphenylmethyl)-4-cyclohexyl-1-hydroxyphenyl acetate ("Pentaacetate")

A 250 milliliter, round bottom flask was charged with 13.37 grams (23.9 mmoles) of 2,6-bis(4-hydroxy-3-(N,N-dimethylaminomethyl)-2,5-dimethylphenylmethyl)-4-cyclohexylphenol and 16.56 grams (162 mmoles) of acetic anhydride. The solution was heated with stirring to reflux and held at reflux for 2 hours. Excess acetic anhydride was removed from the reaction mixture by vacuum distillation. The reaction mixture was cooled in a nitrogen atmosphere to 90° C. 86 mL of methanol were slowly added, and the mixture was refluxed again. The reaction mixture was cooled slowly to 45° C., at which point crystallization occurs. The slurry was cooled to room temperature to precipitate the product. The precipitated product was isolated by filtration, washed with cold methanol, and dried in a vacuum oven.

Part E: Preparation of a 2,6-Bis((4-hydroxy-2,5-hydroxy-4,5-methylenedioxyphenylmethyl)phenylmethyl)-4-cyclohexyl-1-hydroxybenzene A 250 milliliter, round bottom flask was charged with 12.94 grams (18.1 mmoles) pentaacetate, 50 grams (362.3 mmoles) of Sesamol, 160 mL of methanol, 3.33 grams (34 mmoles) concentrated sulfuric acid and 15 mL of water. The solution was heated with stirring to reflux, and held at reflux for 30 hours. 40 mL of methanol were removed from the reaction mixture by distillation. The reaction mixture was cooled to room temperature to precipitate the product. The precipitated product was isolated by filtration, washed with methanol, and dried to constant weight in a vacuum oven.

The product was a mixture of isomers of formula V. Combined, these isomers were 84 are percent pure by HPLC analysis using 80/20 acetonitrile/buffer as eluant.

Preparation of DNQ PAC:

6.0 grams (8.06 mmoles) of 2,6-bis((4-hydroxy-2,5-dimethyl-3-(2-hydroxy-4,5-methylenedioxyphenylmethyl)phenylmethyl)-4-cyclohexyl-1-hydroxybenzene, 4.32 grams (16.08 mmoles) naphthoquinone-(1,2)-diazide-(2)-5-sulfonyl chloride were dissolved in 25 mL of a 50% gamma-butryolactone/acetone solution. Triethylamine was added slowly with stirring so as to maintain a pH of the reaction mixture between 6.0–7.0. Completion of the reaction was determined by the disappearance of the starting naphthoquinone-(1,2)-diazide-(2)-5-sulfonyl chloride. The reaction mixture was acidified to pH=5 by addition of acetic acid. The reaction mixture was added to a solution of 250 mL water and 1.0 mL 37% aqueous hydrochloric acid to precipitate the product. The resulting precipitate was collected by filtration, washed with fresh water, and dried at 25–30° C. under vacuum. The resulting product was a mixture of isomers and was shown by EPLC to be 85% selectively esterified only on the two terminal hydroxyls. The structure of this compound corresponds to the following formula:

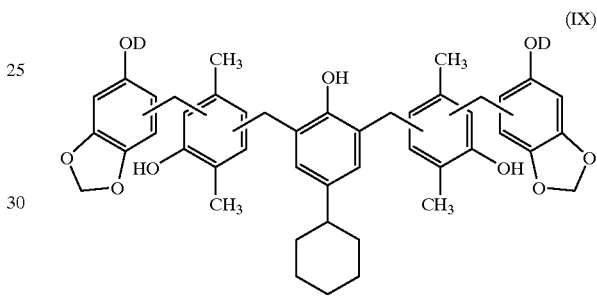

where each D is hydrogen or

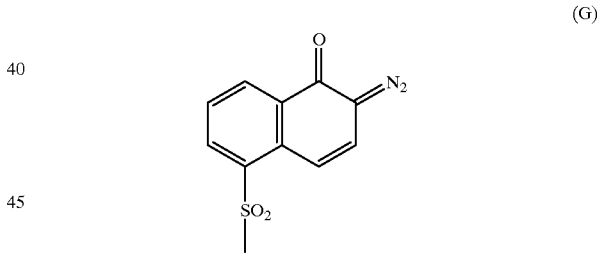

EXAMPLE 3

Preparation of Bis(4-hydroxy-2,5-dimethyl-3-(2-hydroxy-4,5-methylenedioxy-phenylmethyl)phenyl)methane Part A: Preparation of Bis(4-hydroxy-2,5-dimethylphenyl)-methane A 3 liter, round bottom flask was charged with 440 grams (3.6 moles) of 2,5-xylenol, and 450 mL of methanol, 72.9 grams 37% aqueous formalin solution, and 27 grams 37% aqueous hydrochloric acid. The solution was heated with stirring to 80° C. and held at that temperature for 5 hours. The reaction mixture was cooled to room temperature. The mixture was divided into 4 equal portions. Each portion was added to 3 liters of water to precipitate solid compounds. The combined precipitated solids were isolated by filtration and air-dried. The solids were reslurried for 16–24 hours in a solvent mixture consisting of 2.7 liters hexane and 900 milliliters of methylene chloride. The solids were collected by filtration, washed with 900 milliliters of a mixture of 3 parts hexane and 1 part methylene chloride, and air-dried.

The dried solids were dissolved in 870 milliliters of ethanol at 50–55° C. 800 mL of water were slowly added to the ethanol solution, and the solution was cooled to room temperature. The precipitated solids were collected by filtration and dried in a vacuum oven to constant weight.

The product was 93.1 area percent pure by HPLC analysis using 60/40 acetonitrile/buffer as eluant.

Part B: Preparation of Bis(4-hydroxy-3-(N,N-dimethylaminomethyl)-2,5 dimethylphenyl)methane A 1 liter, round bottom flask was charged with 225.3 g (2.0 moles) of 40% aqueous solution of dimethylamine. The contents of the flask were cooled in an ice/water bath, and 63.22 g (2.0 moles) of paraformaldehyde were added in portions while maintaining a reaction temperature of 15° C.–20° C. The reaction mixture was stirred under these conditions for 5 hours, after which the solution of dimethylaminomethanol was filtered.

The dimethylaminomethanol was then added to a 1 liter, round bottom flask charged with 46.97 g (0.1833 moles) of bis(4-hydroxy-2,5-dimethylphenyl)methane and 350 mL of p-dioxane. The mixture was stirred for 16 hours at room temperature, and the precipitated product was isolated by filtration, washed with dioxane, and air-dried.

Part C: Preparation of (2,6-bis(4-acetoxy-3-(acetoxymethyl)-2,5-dimethylphenyl)methane ("Tetraacetate")

A 250 milliliter, round bottom flask was charged with 6.0 g (0.1624 moles) of bis(4-hydroxy-3-N,N-dimethylaminomethyl)-2,5-dimethylphenyl)methane, and 100 mL of acetic anhydride. The solution was heated with stirring to reflux and held at those conditions overnight. Excess acetic anhydride was removed from the reaction mixture by vacuum distillation, and the reaction mixture was cooled under a nitrogen atmosphere. 150 mL of methanol were then slowly added, and the reaction mixture was again refluxed.

The reaction mixture was then cooled slowly to 45° C., at which point crystallization occurs. The slurry was cooled to room temperature, and the precipitated product was isolated by filtration, washed with cold methanol, and dried in a vacuum oven.

Part D: Bis(4-hydroxy-2,5-dimethyl-3-(2-hydroxy-4,5-methylenedioxyphenylmethyl)phenyl)methane A 1000 milliliter round bottom flask was charged with 28.39 g (58.7 mmoles) "tetraacetate", 160 g (1158.4 mmoles) sesamol, and 500 mL of methanol. The solution was heated with stirring to reflux, and 11.38 grams of concentrated sulfuric acid were added. The mixture was refluxed overnight, and then cooled in an ice/water bath. The precipitated product was isolated by filtration, and washed with cold methanol. The solids were dissolved in 150 mL of 1,4-dioxane, filtered, and the filtrate was added into a solution of 1200 mL water and 20 mL 37% aqueous hydrochloric acid. The resulting precipitate was collected by filtration, washed with fresh water and dried at 45–50° C. under vacuum.

The product was 94–95 area percent pure by EPLC analysis using 62/38 acetonitrile/buffer as eluant. $^1$H NMR was consistent with the structure shown below (where D=H).

Preparation of DNQ PAC:

7.5 g (13.47 mmoles) of bis(4-hydroxy-2,5-dimethyl-3-(2-hydroxy-4,5-methylenedioxyphenylmethyl)phenyl)methane, 7.24 g (26.94 mmoles) naphthoquinone-(1,2)-diazide-(2)-5-sulfonyl chloride was dissolved in 100 mL of a 50% γ-butyrolactone/acetone solution. Triethylamine was slowly added with stirring so as to maintain a pH of the reaction mixture between 6.5–8.3. Completion of the reaction was determined by the disappearance of the starting naphthoquinone-(1,2)-diazide-(2)-5-sulfonyl chloride by HPLC. The reaction mixture was acidified to pH=4.6 by addition of acetic acid, and the reaction mixture was then added to a solution of 1800 mL water and 18 mL of 37% aqueous hydrochloric acid. The resulting precipitate was collected by filtration, washed with 1500 mL water and dried under vacuum. The resulting compound was shown by HPLC to be 87–88% selectively esterified only on the two terminal hydroxyls. The structure of this compound corresponds to the following formula (VIII'):

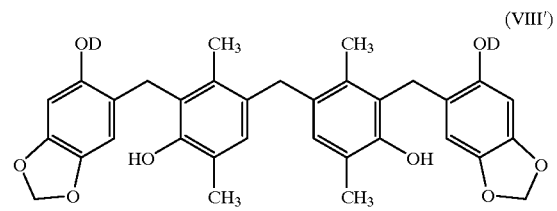

wherein each D is

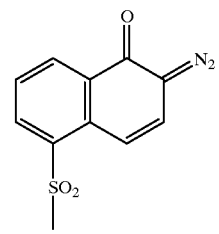

EXAMPLE 4

Preparation of 1,1-bis(4-hydroxy-3-methyl-5-(2-hydroxy-4,5-methylenedioxyphenylmethyl)phenyl)-2,2-dimethylpropane Part A: Preparation of 1,1-bis(4-hydroxy-3-methylphenyl)-2,2-dimethylpropane A 250 mL round bottom flask was charged with 108.14 grams (1.0 moles) of o-cresol, 2.58 grams (0.026 moles) methanesulfonic acid, and 2 grams (0.021 moles) mercaptoacetic acid. The mixture was stirred at room temperature until complete dissolution was obtained. 34.46 grams (0.4 moles) pivaldehyde were then added over 5 minutes. The reaction mixture was heated with stirring to 55–57° C. and held at this temperature for 19 hours. 200 mL toluene and 50 mL water was then added to the reaction mixture which was held at 55–57° C. After 15 minutes, the lower aqueous layer was removed. 50 mL water were again added to the reaction mixture which was held at 55–57° C. After 15 minutes, the lower aqueous layer was removed. The organic layer was then added while warm to 400 mL of hexane. The resulting slurry was then allowed to cool to room temperature. The precipitated solids were isolated by filtration, and washed with a mixture of 60 mL hexane and 30 mL toluene. The solids were air-dried.

The product was 96–98 percent pure by HPLC analysis using 62/38 Acetonitrile/bufer as eluant.

Part B: Preparation of 1,1-bis(4-hydroxy-3-methyl-5-(N,N-dimethylaminomethyl)phenyl)-2,2-dimethylpropane A 500 mL, round bottom flask was charged with 92.3 grams (0.325 moles) of 1,1-bis(4-hydroxy-3-methylphenyl)-2,2-dimethylpropane and 342 mL of ethanol.

A 2000 mL round bottom flask was charged with 105.82 grams (3.53 moles) paraformaldehyde, and 481 mL ethanol. To this slurry was added 396.8 grams (3.53 moles) of 40% aqueous solution of dimethylamine. The solution of 1,1-bis(4-hydroxy-3-methylphenyl)-2,2-dimethylpropane was then added over 3.5 hours. During this addition, the reaction temperature rose to 75° C. External cooling was applied so as to maintain the temperature between 30–50° C. The reaction mixture was stirred overnight at room temperature. Crystallization of the product was induced by addition of a seed crystal. The resulting slurry was stirred for 7.5 hours. The precipitated product was isolated by filtration, and air-dried at room temperature, affording 14.3 grams of product.

Part C: Preparation of 1,1-bis(4-acetoxy-3-methyl-5-acetoxymethylphenyl)-2,2-dimethylpropane A 3000 mL round bottom flask was charged with 56.25 grams 1,1-bis(4-hydroxy-3-methyl-5-(n,N-dimethylaminomethyl)phenyl)-2,2-dimethylpropane, and 2063 mL of acetic anhydride. The solution was stirred at room temperature for 4 hours, then heated with stirring to reflux and held at that those conditions overnight. Excess acetic anhydride was removed from the reaction mixture by atmospheric distillation followed by vacuum distillation. The reaction mixture was cooled under a nitrogen atmosphere. 425 mL of methanol were then added slowly, and the slurry was cooled to room temperature and agitated for at least 1 hour. The precipitated product was isolated by filtration, washed with 304 mL cold methanol, and air-dried at room temperature, affording 56.39 grams of product.

Part D: Preparation of 1,1-bis(4-hydroxy-3-methyl-5-(2-hydroxy-4,5-methylenedioxyphenylmethyl)phenyl)-2,2-dimethylpropane A 1000 milliliter, round bottom flask was charged with 24.0 grams (50 mmoles) 1,1-bis(4-acetoxy-3-methyl-5-acetoxymethylphenyl)-2,2-dimethylpropane, 138.1 grams (1000 mmoles) sesamol, and 400 mL of methanol. The solution was heated with stirring to reflux. A mixture of 9 grams of concentrated sulfuric acid in 33 mL water was added, refluxed for 8 hours, and then cooled to room temperature. 650 mL additional methanol were added to dissolve solids which have precipitated. The methanol solution was then slowly added to a stirred solution consisting of 6500 mL water and 65 grams of concentrated aqueous hydrochloric acid. The precipitated product was isolated by filtration, and washed with cold methanol. The solids were extracted for 1 hour with 2000 mL of refluxing water. The water was decanted from the solid, and the solids were extracted overnight with 2000 mL of refluxing water. The water was again decanted, and the solids were collected by filtration, washed with 200 mL water, and dried at 45–50° C. under vacuum. The product was 95 area percent pure by HPLC analysis using 80/20 acetonitrile/buffer as eluant. $^1$H-NMR analysis was consistent with the structure shown below (where D=H).

Preparation of DNQ PAC:

5.86 grams (10 mmoles) of 1,1-bis(4-hydroxy-3-methyl-5-(2-hydroxy-4,5-methylenedioxyphenylmethyl)phenyl)-2,2-dimethylpropane, and 5.374 grams (20 mmoles) naphthoquinone-(1,2)-diazide-(2)-5 sulfonyl chloride were dissolved in 75 mL of a 50% γ-butyrolactone/acetone solution. 2.03 grams (20 mmoles) triethylamine were slowly added with stirring so as to maintain a pH of the reaction mixture below 8.0. Completion of the reaction was determined by the disappearance of the starting naphthoquinone-(1,2)-diazide-(2)-5-sulfonyl chloride by RPLC. 5.86 grams of water were then added, and the reaction mixture was acidified to pH=4.6 by addition of acetic acid. The reaction mixture was then added to 2344 mL water to precipitate solids. The resulting precipitate was collected by filtration, washed with 1172 mL water and dried under vacuum.

The resulting compound was shown by HPLC to be 97–98% selectively esterified only on the two terminal hydroxyls. The structure of this compound corresponds to the following formula (X'):

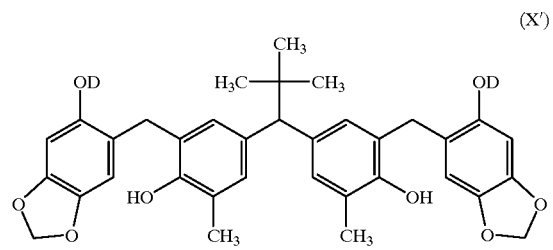

wherein each D is

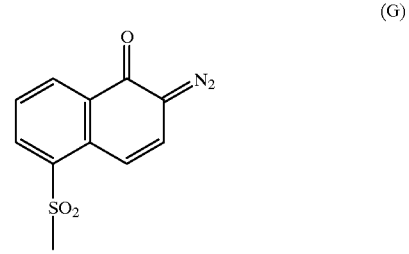

Preparation of Novolak No. 1

Novolak No. 1 was prepared by the procedures previously described in U.S. Pat. No. 5,346,808. The following monomer mixtures were used:

| Monomer | Amount (%, w/w) |
| --- | --- |
| 2,2'-dihydroxy-5,5-dimethyldiphenylmethane | 4.59 |
| o-cresol | 1.73 |
| 2,3-dimethylphenol | 63.9 |
| 2,3,5-trimethylphenol | 21.92 |
| 2,6-dimethylphenol | 7.88 |

A formaldehyde/monomer molar ratio of 1.16 was used in the preparation of Novolak No. 1. The weight average molecular weight (Mw) of Novolak No. 1, as determined by Gel Permeation Chromatography, was 2,865. GPC results are relative to polystyrene standards.

Preparation of Novolak No. 2

Novolak No. 2 was prepared by the procedures previously described in U.S. Pat. No. 4,529,682. The following monomer mixtures were used:

| Monomer | Amount (%, w/w) |
|---|---|
| p-cresol | 60% |
| m-cresol | 40% |

Formaldehyde/monomer molar ratios of 0.62–0.65 were used in the preparation of Novolak No. 2. The weight average molecular weight (Mw) of Novolak No. 2, as determined by Gel Permeation Chromatography, varied from 5,000–7,000. GPC results are relative to polystyrene standards.

Speed Enhancer A

Speed Enhancer A is 1,3,3',5-tetra-(4-p-hydroxyphenyl)pentane (THPP). Its chemical structure is shown by formula (Q), above.

EXAMPLES 5–18

Preparation of Photoresists

Fourteen (14) photoresist formulations were prepared from the photoactive compounds of Examples 2, 3 or 4; novolaks Nos. 1 and 2, and in some cases, Speed Enhancer A. A leveling agent, FC-430 FLUORAD, made by 3M of St. Paul, Minn., was added to all formulations at a concentration of 0.03% by weight, based on total of the formulation. A solvent mixture of 70% by weight ethyl lactate and 30% by weight ethyl-3-ethoxypropionate was used in all formulations. The solids % in each resist formulation was 25%.

Each resist solution is micro filtered through a $0.2\mu$ pore size filter made by Pall Corporation, Long Island, N.Y. The following are the exact ratios of the components of each resist formulation expressed in weight percent based on the solids (excluding the solvents weight). In Table 1 below, percentages of each component for these 14 photoresist formulations is provided on the solids weight amount alone (excluding the solvents weight):

TABLE 1

| Example No. | Total PAC wt. % | PAC system (% by weight of total PACs in blend) | | Novolak | Speed Enhancer (Formula Q) wt. % |
|---|---|---|---|---|---|
| | | PAC 1 (see footnote 1) | PAC 2 | | |
| 5 | 40.0 | 100% Formula VIII (esterification level = 2S) | | Novolak 1 | 15.0 |
| 6 | 34.0 | 100% Formula VIII (esterification level = 2.3S) | | Novolak 1 | 14.52 |
| 7 | 26.5 | 50% Formula VIII (esterification level = 2.3S) | 50% compound (K) (see footnote 2) | Novolak 1 | 12.13 |
| 8 | 27.5 | 52% Formula VIII (esterification level = 2.0S) | 48% compound (K) | Novolak 1 | 11.96 |
| 9 | 32.0 | 50% Formula VIII (esterification level = 2.0S) | 50% compound (K) | Novolak 1 | 13.6 |
| 10 | 40.0 | 70% Formula VIII (esterification level 2.0S) | 30% compound (K) | Novolak 1 | 15.0 |
| 11 | 23.7 | 100% Formula VIII (esterification level = 2.0S) | | Novolak 2 | 0 |
| 12 | 32.0 | 100% Formula X (70% esterification level = 3.0S 30% esterification level = 2.0S) | | Novolak 1 | 13.6 |
| 13 | 37.0 | 100% Formula X (esterification level = 2.0S) | | Novolak 1 | 15.75 |
| 14 | 32.0 | 100% Formula X (70% esterification level = 3.0S 30% esterification level = 2.0S) | | Novolak 1 | 13.6 |
| 15 | 27.9 | 52% Formula X (esterification level = 2.0S) | 48% compound (K) | Novolak 1 | 11.9 |
| 16 | 24.0 | 100% Formula X (esterification level = 3.0S) | | Novolak 2 | 0 |
| 17 | 39.8 | 100% Formula IX (esterification level = 2.0S) | | Novolak 1 | 15.05 |

TABLE 1-continued

| Example No. | Total PAC wt. % | PAC system (% by weight of total PACs in blend) | | | Speed Enhancer (Formula Q) wt. % |
| --- | --- | --- | --- | --- | --- |
| | | PAC 1 (see footnote 1) | PAC 2 | Novolak | |
| 18 | 16.8 | 44% Formula IX (esterification level = 2.0S) | 56% compound (K) | Novolak 1 | 13.73 |

Footnotes to Table 1:
1) Esterification level represents the mole ratio between 2,1-diazonaphthoquinone-5-sulfonyl chloride and the backbone of interest. Thus in example 5, Formula VIII with an esterification level of 2.0S was obtained by esterifying one mole of bis(4-hydroxy-2,5-dimethyl-3-(2-hydroxy-4,5-methylenedioxyphenylmethyl)phenyl)methane (Formula VIII) with 2 moles of 2,1-diazonaphthoquinone-5-sulfonyl chloride according to the procedure previously described.
2) The DNQ ester of compound K was obtained by esterifying one mole of bis(3,5-dimethyl-4-hydroxyphenyl)-3-methoxy-4-hydroxyphenylmethane with about 2.6 moles of 2,1-diazonaphthoquinone-5-sulfonyl chloride. The DNQ ester of compound K contained about 61–66% D3 ester as determined by HPLC analysis.

Coating, Softbaking, Exposure, Post Exposure Baking and Developing of the Photoresist Films of the formulated photoresists were prepared for imaging, exposed, and developed according to the following general procedure: The wafers were spin coated by applying 3 ml of photoresist formulations shown in TABLE 1 to the static wafer. The wafer was then spun at 500 rpm to spread the resist, and finally at 3,000 to 6,000 rpm to give 1.03 micron and 0.97 micron films, respectively. These photoresist coated wafers were then softbaked on a vacuum chuck hot plate at 90° C. for 60 seconds to remove residual solvent. The softbaked photoresist coated wafers were exposed for lithographic evaluation properties, as well as the dissolution rate properties.

The dissolution properties and the lithographic properties were measured by exposing the softbaked wafers to 365 NM light (I-line) using a Canon stepper with a numerical aperture of 0.52. The exposure energy was controlled by the time a shutter was open allowing the light to strike the photoresist film.

After completion of exposure, the wafers were subjected to a post exposure bake (PEB) to lessen or remove the standing waves from the exposure. This was done using the vacuum chuck hot plate at 110° C. for 60 seconds. Following the PEB, the wafers were puddle-developed using 0.262N tetramethylammonium hydroxide, aqueous developer. A Perkin Elmer Development rate monitor was used to measure the dissolution rate of the exposed and unexposed areas using the same developer in a static immersion mode. The wafers exposed for lithographic evaluation were developed using a track system. The wafer remained stationary for 60 seconds while development occurred. A deionized water rinse was applied for 20 seconds while spinning, followed by dry nitrogen gas to dry the wafer. The wafer was then ready for lithographic evaluation.

Each imaged photoresist-coated substrate was evaluated for several important properties, namely the exposure threshold (Eth); Optimum photospeed (Eopt); equal line/space pair resolution (Res.); depth-of-focus of 0.40 micron line/space pairs (DOF).

Eth was measured on exposed wafers using small exposure increments on large unpatterned areas printed across the wafer. The clearing dose for the resist film was determined visually.

The resist photospeed, resolution, and depth of focus (DOF) were evaluated by means of a scanning electron microscope.

The optimum exposure energy (Eopt) was determined as the energy required to replicate the dimensions of the mask for 0.5 micron line/space pairs.

The resolving power (Res.) of the photoresist film is determined as the minimum line/space pair features which are cleared at the Eopt. The resolved features were reported in microns. Generally, the lower the resolution values, the better the resist performed.

The depth-of-focus (DOF) is a measure of the focus latitude of the photoresist corresponding to a change in the best focus used to create an image. When the focal plane of projected images is shifted above and below the resist plane, the line/space pairs created in the photoresist become deformed, due to the poor aerial image. The total range (microns), in which the focus can vary and still have acceptable critical dimensions, is defined as the DOF.

Photoresist Evaluations

The lithographic properties of these photoresists were evaluated. The results of this evaluation at various soft bake film thicknesses are provided in TABLE 2.

TABLE 2

| Example No. | Resolution in $\mu$ | Depth of focus for $0.4\mu$ features in $\mu$ | Eopt mJ/cm$^2$ | Eth mJ/cm$^2$ |
| --- | --- | --- | --- | --- |
| 5 | 0.33 | >1.6 | 240 | 109 |
| 6 | 0.33 | 1.2 | 190 | 98 |
| 7 | 0.33 | 1.6 | 235 | 107 |
| 8 | 0.32 | 1.5 | 245 | 107 |
| 9 | 1.35 | 1.8 | 267 | 128 |
| 10 | 1.35 | 1.8 | 322 | 140 |
| 11 | 0.37 | 1.2 | 147 | 86 |
| 12 | 0.32 | 1.8 | 260 | 98 |
| 13 | 0.33 | 1.6 | 124 | 59 |
| 14 | 0.35 | 1.8 | 230 | 110 |
| 15 | 0.35 | 1.5 | 176 | 89 |
| 16 | 0.35 | 1.8 | 293 | 149 |
| 17 | 0.32 | 2.0 | 420 | 179 |
| 18 | 0.40 | 0.6 | 147 | 89 |

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A process of forming a positive patterned image on a substrate, comprising the steps of:

(1) coating said substrate with a radiation sensitive mixture useful as a positive working photoresist, said mixture comprising an admixture of an alkali soluble binder resin and at least one photosensitive compound comprising at least one o-quinonediazide sulfonic acid ester of a phenol compound, said ester having formula (II):

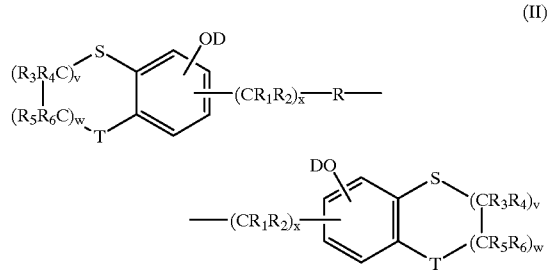

wherein $R_1, R_2, R_3, R_4, R_5$, and $R_6$ are each independently selected from the group consisting of H and a lower alkyl group having 1–4 carbon atoms;

v and w are each an integer from 0 to 2 with the proviso that v and w cannot simultaneously be 0;

each S and T are independently selected from the group consisting of oxygen and —$CH_2$—, with the proviso that S and T cannot simultaneously be —$CH_2$—;

X is an integer from 1–4;

R is a bivalent alkali-soluble moiety selected from the formulae (A'), (B'), (C'), (D'), and (E'):

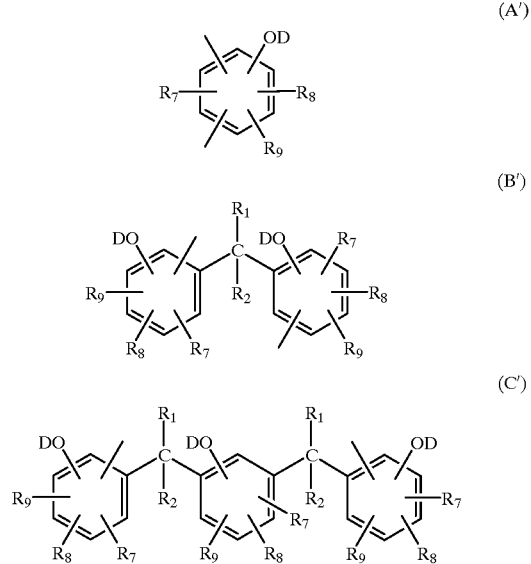

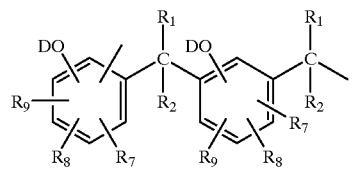

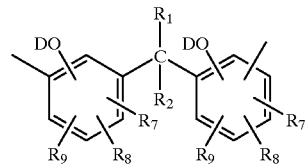

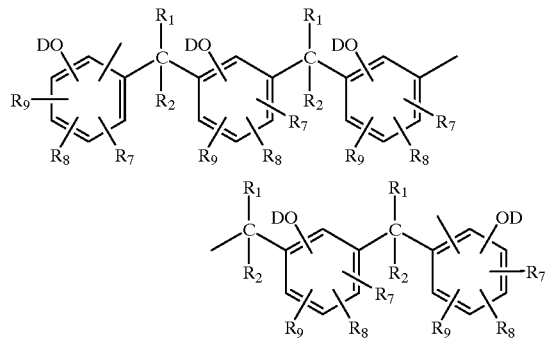

wherein $R_7$, $R_8$, and $R_9$ are independently selected from the group consisting of hydrogen, lower alkyl groups having 1–4 carbon atoms, araalkyl and cycloalkyl; and OD is either hydrogen or an o-quinonediazide sulfonic acid ester group, subject to the proviso that not all Ds are hydrogen and at least about 75% of the hydroxyl groups on said phenolic rings having the cyclic ether moieties have been esterified with an o-quinonediazide sulfonic acid moiety, and less than about 25% of the hydroxyl groups on phenolic rings having no cyclic ether moieties have been esterified;

wherein the amount of said photosensitive compound is from about 5% to about 40% by weight, based on the total solid content of said radiation sensitive mixture;

(2) subjecting said coating on said substrate to an image-wise exposure of radiation; and (3) subjecting said image-wise exposed coated substrate to a developing solution wherein the exposed area of said radiation-exposed coatings are dissolved and removed from the substrate, thereby resulting in positive image-wise pattern in the coating.

2. The process of claim 1, wherein said radiation is ultraviolet light.

3. The process of claim 1, wherein said image-wise exposed coated substrate is subjected to a post exposure bake at a temperature from about 100° C. to about 130° C. before said development step (3).

4. The process of claim 1, wherein said developing solution comprises an aqueous solution of an alkali metal hydroxide or silicates or an aqueous solution of tetramethylammonium hydroxide.

5. The process of claim 1, wherein said photosensitive compound is present in the amount of about 8% to about 30% by weight, based on the total solid content of said radiation-sensitive mixture.

6. The process of claim 1, wherein D is naphthoquinone-(1,2)-diazide-(2)-5-sulfonyl; naphthoquinone-(1,2)-diazide-(2)-4-sulfonyl or hydrogen.

7. The process of claim 1, wherein at least 80% of said phenolic rings with said cyclic ether moiety thereon are esterified with an o-quinonediazide sulfonic acid moiety.

8. The process of claim 1, wherein D is naphthoquinone-(1,2)-diazide-(2)-5-sulfonyl or naphthoquinone-(1,2)-diazide-(2)-4-sulfonyl.

9. The process of claim 1, wherein said substrate comprises one or more compounds selected from the group consisting of polyester, polyolefin, silicon, gallium arsenide, silicon/silicon dioxide, doped silicon dioxide, silicon nitride, aluminum/copper mixtures, tantalum, copper, and polysilicon.

10. The process of claim 1, wherein said substrate is a silicon wafer coated with silicon dioxide.

* * * * *